United States Patent [19]
Bonaldi et al.

[11] 4,316,849
[45] Feb. 23, 1982

[54] PROCESS FOR PREPARING A CRYSTALLINE POLYMORPHOUS TYPE OF CHENODEOXYCHOLIC ACID

[75] Inventors: Antonio Bonaldi, Schilpario; Egidio Molinari, Erba, both of Italy

[73] Assignee: Blasinachim S.p.A., Milan, Italy

[21] Appl. No.: 167,469

[22] Filed: Jul. 11, 1980

[30] Foreign Application Priority Data

Jul. 12, 1979 [IT] Italy ............................... 24317 A/79

[51] Int. Cl.$^3$ ................................................ C07J 9/00
[52] U.S. Cl. ................................................. 260/397.1
[58] Field of Search ..................................... 260/397.1

[56] References Cited

U.S. PATENT DOCUMENTS 4,163,017  7/1979  Maeke et al. .................. 260/397.1
4,213,911  7/1980  Attwell et al. ................. 260/397.1

Primary Examiner—Elbert L. Roberts
Attorney, Agent, or Firm—Stevens, Davis, Miller & Mosher

[57] ABSTRACT

The humid amorphous form of chenodeoxycholic acid undergoes a physical treatment at room temperature comprising causing a collision of the particles of the amorphous product in bulk by means of shaking or stirring to prepare the solvent-free crystalline form of chenodeoxycholic acid which melts at 168°–170° C.

4 Claims, No Drawings

PROCESS FOR PREPARING A CRYSTALLINE POLYMORPHOUS TYPE OF CHENODEOXYCHOLIC ACID

This invention relates to a method for preparing the crystalline polymorphous type of Chenodeoxycholic acid which melts at 168°–170° C. More particularly, it relates to a method for converting quantitatively the amorphous form of chenodeoxycholic acid into the corresponding crystalline form melting at 168°–170° C., pure and free from solvents.

It is known (Il Farmaco, Ediz. Scient. 33, 64, 1978) that chenodeoxycholic acid has, in addition to the amorphous form, also three polymorphous crystalline forms having, respectively, the following melting points: 119° C., 138° C. and 168° C.

Among the three crystalline forms, the last one seems to be the most suitable for preparing finished pharamceutical forms owing to its physical properties i.e. low electrification and small specific volume.

As the crystalline polymorphic form having the highest melting point cannot be obtained directly when chenodeoxycholic acid is manufactured by synthetic route, some methods have been suggested for preparing it by using the other polymorphic forms as starting products.

According to the French open-application No. 2,346,370, the polymorphic form melting at 168°–171° C. is obtained by crystallization of crude chenodeoxycholic acid from acetonitrile. The acid thus obtained contains a certain quantity of acetonitrile. In fact, the crystals of chenodeoxycholic acid have the undesired property that they hold firmly the crystallization-solvent and it is practically impossible to remove it by means of the usual methods. No satisfactory results are obtained either by drying the crystals in an oven under reduced pressure or with a flow of hot and dried air.

The use of chenodeoxycholic acid in the human medicine field as gallstone dissolving agent involves a long-term treatment; in this connection it is a must to use a product which is substantially free from any contaminating agent, inclusive of the crystallization-solvents.

Obviously it is not advisable to use in the human therapeutical field chenodeoxycholic acid which is contaminated by crystallization-solvents like acetonitrile, which are toxic.

The Japanese unexamined open-application No. 78 65867 discloses a method for converting either of the two polymorphic forms melting at 119° C. and 143° C. into the crystalline form having the highest melting point. This method lies in suspending one or both the forms having the lower melting points in an excess of water, preferably from 10 to 50 volumes of water for each part of the product, and in letting the suspension to stand at 60° to 90° C. up to 65 hours.

This method may be carried out on small scale for converting small quantities of the product but it is not suitable for an industrial processing when it is necessary to process large quantities of the product, principally because the starting product needs to be maintained in thin suspension in order to convert it completely, whereas the high temperature required for the transformation favours the aggregation of the crystals. Thus it is obtained a crystalline product which has not the desired properties.

Now, it has been found an easy method that allows to transform completely the amorphous form into the pure crystalline polimorphic form of chenodeoxycholic acid having the highest melting point.

According to the method of this invention, the amorphous form of chenodeoxycholic acid, in the solid state and in the presence of moisture, undergoes a physical treatment at room temperature consisting in causing a continuous collision of the particles by means of mechanical shaking or stirring. This treatment is carried on for 24 to 48 hours in accordance with the quantity of the product to be converted and the effectiveness of the equipment.

As equipment suitable for carrying on the mechanical treatment of this invention may be used a mixer equipped with an Archimedean screw as a stirrer.

According to a preferred embodiment of this invention the product in bulk to be subjected to the physical treatment has a content of water from 10% to 80%.

The following examples are intended only to illustrate but not to limit this invention.

EXAMPLE 1

392 g. of chenodeoxycholic acid melting at 118°–120° C. are dissolved in 4000 ml. of deionized water containing 40 g. of sodium hydroxide. The solution is filtered and then acidified up to pH 2 with 20% sulphuric acid. The precipitate is collected by filtration and washed with deionized water till disappearance of the sulphates.

The humid (68% of water) product in bulk is introduced into a mixer equipped with an Archimedean screw as a stirrer and stirred at room temperature for 48 hours.

The product is discharged and dried in an oven under an air-flow.

Yield, 390 g of chenodeoxycholic acid which melts at 168°–170° C. and is free from solvents (gascromathographic analysis).

EXAMPLE 2

392 g of chenodeoxycholic acid are dissolved at room temperature in 600 ml of methanol. The solution thus obtained is added slowly to 4000 ml of deionized water while the temperature is kept at +2° C.

The precipitate is collected by filtration, washed with water and subjected to the same physical treatment as per example 1.

We claim:

1. A process for preparing crystalline chenodeoxycholic acid melting at about 168–170° C. and free of crystallization solvents, said process consisting essentially of treating humid, amorphous chenodeoxycholic acid at room temperature by shaking or stirring it in bulk so as to cause the particles of the amorphous product to collide, and thereby to assume the desired crystalline form.

2. A process according to claim 1 wherein the water content of the humid amorphous form of chenodeoxycholic acid ranges between 10% and 80%.

3. A process according to claim 1 or 2 wherein said treatment duration ranges from 24 to 48 hours.

4. A process according to claim 1 or 2 wherein said humid amorphous acid is treated by stirring in a mixer equipped with an Archimedean screw.

* * * * *